(12) United States Patent
Birkhold et al.

(10) Patent No.: US 12,406,170 B2
(45) Date of Patent: Sep. 2, 2025

(54) PROVISION OF AT LEAST ONE PROCEDURE PARAMETER

(71) Applicant: Siemens Healthcare GmbH, Erlangen (DE)

(72) Inventors: Annette Birkhold, Stuttgart (DE); Philipp Roser, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 20 days.

(21) Appl. No.: 18/140,866

(22) Filed: Apr. 28, 2023

(65) Prior Publication Data
US 2023/0352143 A1 Nov. 2, 2023

(30) Foreign Application Priority Data

Apr. 28, 2022 (DE) ...................... 10 2022 204 170.4

(51) Int. Cl.
*A61B 34/10* (2016.01)
*G06N 3/045* (2023.01)
*G06N 3/09* (2023.01)

(52) U.S. Cl.
CPC ............ *G06N 3/045* (2023.01); *A61B 34/10* (2016.02); *G06N 3/09* (2023.01);
(Continued)

(58) Field of Classification Search
CPC ... A61B 34/00; A61B 34/10; A61B 2034/101; A61B 2034/102; A61B 2034/104; A61B 2034/105
See application file for complete search history.

(56) References Cited

U.S. PATENT DOCUMENTS

2019/0343588 A1 11/2019 Juergens
2020/0222018 A1 7/2020 Van Walsum et al.
(Continued)

FOREIGN PATENT DOCUMENTS

DE 102018111180 A1 11/2019
DE 102020216011 A1 11/2021

OTHER PUBLICATIONS

Elijovich, Lucas, et al. "Predictors and outcomes of intraprocedural rupture in patients treated for ruptured intracranial aneurysms: the CARAT study." Stroke 39.5 (2008): 1501-1506.
(Continued)

*Primary Examiner* — Joseph M Santos Rodriguez
*Assistant Examiner* — Tommy T Ly
(74) *Attorney, Agent, or Firm* — Lempia Summerfield Katz LLC

(57) ABSTRACT

A method for providing at least one procedure parameter includes acquiring at least one intraprocedural projection map that maps a hollow organ of an examination object with at least one medical object positioned in the hollow organ. A trained function is applied to the at least one intraprocedural projection map as input data. At least one parameter of the trained function is adjusted based on a simulation of a virtual positioning of at least one medical training object in a training hollow organ and of hemodynamics in the training hollow organ that are influenced by the at least one medical training object. The at least one procedure parameter is provided as output data of the trained function. The at least one procedure parameter includes a movement specification for the at least one medical object.

18 Claims, 9 Drawing Sheets

(52) U.S. Cl.
CPC ... *A61B 2034/102* (2016.02); *A61B 2034/104* (2016.02); *A61B 2034/105* (2016.02)

(56) References Cited

U.S. PATENT DOCUMENTS

| | | | |
|---|---|---|---|
| 2021/0287434 A1 | 9/2021 | Wham | |
| 2021/0290308 A1 | 9/2021 | Mihalef et al. | |
| 2022/0395334 A1* | 12/2022 | Meglan | A61B 34/10 |

OTHER PUBLICATIONS

Ihn, Yon Kwon, et al. "Complications of endovascular treatment for intracranial aneurysms: management and prevention." Interventional Neuroradiology 24.3 (2018): 237-245.

Lamano, Jonathan B., et al. "Force characterization of intracranial endovascular embolization: coil type, microcatheter placement, and insertion rate." Neurosurgery 75.6 (2014): 707.

Matsubara, Noriaki, et al. "A novel pressure sensor with an optical system for coil embolization of intracranial aneurysms." Journal of neurosurgery 111.1 (2009): 41-47.

Matsubara, Noriaki, et al. "Evaluation of the characteristics of various types of coils for the embolization of intracranial aneurysms with an optical pressure sensor system." Neuroradiology 53 (2011): 169-175.

Santillan, A., et al. "Intraprocedural aneurysmal rupture during coil embolization of brain aneurysms: role of balloon-assisted coiling." American journal of neuroradiology 33.10 (2012): 2017-2021.

Shintai, Kazunori, et al. "Experimental study of coil delivery wire insertion force in intracranial aneurysm embolization: force discrepancy generated inside the microcatheter through that coil delivery wire passes." Nagoya Journal of Medical Science 81.2 (2019): 217.

Wei, Yiyi, et al. "Interactive blood-coil simulation in real-time during aneurysm embolization." Computers & Graphics 35.2 (2011): 422-430.

Miyachi, Shigeru, et al. "Remote surgery using a neuroendovascular intervention support robot equipped with a sensing function: experimental verification." Asian Journal of Neurosurgery 16.02 (2021): 363-366.

* cited by examiner

ID="1"/>

PROVISION OF AT LEAST ONE PROCEDURE PARAMETER

This application claims the benefit of German Patent Application No. DE 10 2022 204 170.4, filed on Apr. 28, 2022, which is hereby incorporated by reference in its entirety.

BACKGROUND

The present embodiments relates to providing at least one procedure parameter, providing a first neural network, providing a second neural network, and providing a trained function.

Endovascular occlusion of an aneurysm and/or a vessel malformation is frequently demanding and entails correct selection of the microcatheter and implant (e.g., a coil implant, such as with regard to respective rigidity). The correct selection often depends on a geometric characteristic of the aneurysm and/or vessel malformation. In addition, a number of attempts are frequently required in order to position the implant correctly in the aneurysm and/or vessel malformation. As described in the paper by Lamano et al., Neurosurgery, 2014, 75(6), 707-716, the success of endovascular occlusion may depend on a number of different factors (e.g., the type of coil implant, such as with regard to rigidity and/or size, the type of microcatheter, such as with regard to rigidity and/or size, positioning of the microcatheter, insertion rate, insertion force, and/or positioning of the microcatheter). Since two medical objects (e.g., the coil implant and the microcatheter) are to be controlled, the interventional procedure is frequently complex and time-consuming.

Disadvantages of endovascular occlusion include various risks to the aneurysm and/or vessel malformation (e.g., thromboembolic events, intraoperative ruptures and/or overpacking). In addition, external (e.g., nonlinear) disruptive factors (e.g., due to blood flow) and robustness frequently constitute possible significant challenges for a coiling procedure.

SUMMARY AND DESCRIPTION

The scope of the present invention is defined solely by the appended claims and is not affected to any degree by the statements within this summary.

The present embodiments may obviate one or more of the drawbacks or limitations in the related art. For example, improved selection and/or control of medical objects in interventional procedures is provided.

The solution according to the present embodiments is described below not only with respect to methods and apparatuses for providing at least one procedure parameter but also with respect to methods and apparatuses for providing a trained function and a first neural network or a second neural network. Features, advantages, and alternative embodiments of data structures and/or functions in methods and apparatuses for providing at least one procedure parameter may, for example, be transferred to analogous data structures and/or functions in methods and apparatuses for providing a trained function, a first neural network, or a second neural network. Analogous data structures may, for example, be characterized by the use of the qualifier "training". Further, the trained function, the first neural network, and/or the second neural network used in methods and apparatuses for providing at least one procedure parameter may also have been provided by the corresponding methods.

A first aspect of the present embodiments relates to a method for providing at least one procedure parameter. In a first act a), at least one intraprocedural projection map that maps a hollow organ of an examination object with at least one medical object positioned in the hollow organ is acquired. In a second act b), a trained function is applied to the at least one intraprocedural projection map as input data. The at least one procedure parameter includes, for example, a movement specification for the at least one medical object. In addition, at least one parameter of the trained function is adjusted based on a simulation of a virtual positioning of at least one medical training object in a training hollow organ and of the hemodynamics in the training hollow organ that are influenced by the at least one medical training object. The at least one procedure parameter is provided as output data of the trained function.

Acquisition of the at least one intraprocedural projection map may include capturing and/or receiving the at least one intraprocedural projection map. For example, a plurality of intraprocedural projection maps that map the hollow organ with the at least one medical object positioned in the hollow organ may be acquired.

The at least one intraprocedural projection map may be captured via a medical imaging device. The medical imaging device for capturing the at least one intraprocedural projection map may take the form of a medical X-ray device (e.g., medical C-arm X-ray device) and/or computed tomography system (CT system). The at least one intraprocedural projection map may, for example, include at least one intraprocedural X-ray projection map.

Receiving the at least one intraprocedural projection map may, for example, include acquiring and/or reading out a computer-readable data memory and/or receiving from a data storage unit (e.g., a database). Further, the at least one intraprocedural projection map may be provided by a provision unit of a medical imaging device.

The at least one intraprocedural projection map may include a two-dimensional (2D) spatially resolved map of the hollow organ of the examination object with the at least one medical object positioned in the hollow organ. For example, the at least one intraprocedural projection map may intraprocedurally map the hollow organ of the examination object with the at least one medical object positioned in the hollow organ. If a plurality of intraprocedural projection maps are acquired, the plurality of intraprocedural projection maps may map the hollow organ of the examination object with the at least one medical object positioned in the hollow organ in temporally resolved manner. In one embodiment, the plurality of intraprocedural projection maps may be captured (e.g., in temporal succession) with a substantially identical capture geometry with regard to the examination object.

The examination object may, for example, be a human and/or animal patient. The at least one medical object may, for example, include a diagnostic and/or surgical instrument (e.g., a guide wire and/or a microwire and/or a catheter) and/or an implant (e.g., a stent) and/or a, for example, mechanical and/or chemical embolizate.

The trained function may be trained by a machine learning method. For example, the trained function may be a neural network (e.g., a convolutional neural network (CNN) or a network including a convolutional layer).

The trained function maps input data onto output data. The output data may, for example, be dependent on one or more parameters of the trained function. The one or more parameters of the trained function may be determined and/or adjusted by training. Determination and/or adjustment of the one or more parameters of the trained function may, for example, be based on a pair of training input data and associated training output data (e.g., comparison output data). The trained function is applied to the training input data to produce training map data. For example, determination and/or adjustment may be based on a comparison of the training map data and the training output data (e.g., comparison output data). In general, a trainable function (e.g., a function with one or more parameters that are not as yet adjusted) is also denoted a trained function.

Other terms for trained functions are trained mapping rule, mapping rule with trained parameters, function with trained parameters, algorithm based on artificial intelligence, or machine learning algorithm. One example of a trained function is an artificial neural network, where the edge weights of the artificial neural network correspond to the parameters of the trained function. The term "neural net" may also be used instead of the term "neural network". For example, a trained function may also be a deep artificial neural network or deep neural network. Another example of a trained function is a "support vector machine," while other machine learning algorithms may, for example, also be used as a trained function.

The trained function may, for example, be trained via backpropagation. First of all, training map data may be determined by applying the trained function to training input data. A deviation between the training map data and the training output data (e.g., the comparison output data) may then be ascertained by applying an error function to the training map data and the training output data (e.g., the comparison output data). Further, at least one parameter (e.g., a weighting) of the trained function (e.g., of the neural network) may be iteratively adjusted based on a gradient of the error function with regard to the at least one parameter of the trained function. In this way, the deviation between the training map data and the training output data (e.g., the comparison output data) may be minimized during training of the trained function.

The trained function (e.g., the neural network) may have an input layer and an output layer. The input layer may, for example, be configured to receive input data. The output layer may also be configured to provide map data (e.g., output data). The input layer and/or the output layer may, for example, in each case, include a plurality of channels (e.g., neurons).

The input data of the trained function may be based on the at least one intraprocedural projection map. For example, the input data of the trained function may include the at least one intraprocedural projection map. The trained function may also provide the at least one procedure parameter (e.g., a plurality of procedure parameters).

At least one parameter of the trained function may be adjusted based on the simulation of the virtual positioning of the at least one medical training object in the training hollow organ and of the hemodynamics in the training hollow organ, which are influenced by the at least one medical training object. For example, the trained function may be provided by an embodiment of the method for providing a trained function and/or of the further method for providing a trained function, which methods are described below.

The at least one procedure parameter includes a movement specification for the at least one medical object. The movement specification may, for example, specify at least one parameter (e.g., a plurality of parameters) of a future movement of the at least one medical object. Provision of the at least one procedure parameter may include storage on a computer-readable storage medium and/or display on a display unit and/or transfer to a provision unit and/or transfer to a movement apparatus for robotic movement of the at least one medical object. For example, a graphical representation (e.g., a workflow instruction) of the at least one procedure parameter may be displayed via the display unit.

The embodiment (e.g., the at least one provided procedure parameter) may enable improved selection and/or control of the at least one medical object (e.g., improved selection of the at least one medical object to be controlled and/or moved). In addition, the embodiment may enable efficient (e.g., computationally efficient and/or time-efficient and/or dose-efficient) and at the same time accurate provision of the at least one procedure parameter. In addition, the embodiment may enable intraprocedural provision of the at least one procedure parameter (e.g., in real time and/or online).

In a further embodiment of the method for providing at least one procedure parameter, the at least one intraprocedural projection map may map a plurality of medical objects that are positioned in the hollow organ. The least one procedure parameter may also include a movement specification for the plurality of medical objects.

The plurality of medical objects may be of at least partially (e.g., completely) identical or different construction. The plurality of medical objects may be positioned (e.g., intraprocedurally) in the hollow organ during capture of the at least one intraprocedural projection map. The plurality of medical objects may, for example, be chemically and/or mechanically and/or electromagnetically interactive and/or collaborative. One medical object of the plurality of medical objects may, for example, be configured to introduce, deploy, and/or position a further medical object of the plurality of medical objects.

The at least one parameter of the trained function may be adjusted based on a simulation of a virtual positioning of a plurality of medical training objects in the training hollow organ and of the hemodynamics in the training hollow organ that are influenced by the plurality of medical training objects. Further, the at least one procedure parameter may in each case include a movement specification for the plurality of medical objects.

Improved (e.g., coordinated) selection and/or control of the plurality of medical objects may be enabled in this way.

In a further embodiment of the method for providing at least one procedure parameter, the at least one medical object may include a microcatheter and/or a coil implant.

The microcatheter may have a diameter of a few millimeters (e.g., between 0.7 mm and 1.3 mm). The microcatheter may be configured to be navigated through complex and/or distal vascular structures. The microcatheter may be configured for introducing and/or deploying a, for example, therapeutic (e.g., mechanical and/or chemical) embolizate and/or contrast agent and/or coil implant.

The coil implant may include one or more wires that are configured to be introduced into a portion of the hollow organ (e.g., an aneurysm and/or a vessel malformation). In addition, the coil implant may be configured, once introduced into the portion of the hollow organ (e.g., the aneurysm and/or vessel malformation) to adopt a predefined pose (e.g., a spiral and/or loop), such that occlusion of the portion of the hollow organ is enabled. The simulation of the virtual positioning of the at least one medical training object may include a coiling simulation (e.g., based on a coiling model) to obtain a pose of the at least one medical training object. The simulation of the virtual positioning (e.g., the coiling simulation) may, for example, include a simulation of an interaction between the at least one medical training object and the training hollow organ.

The microcatheter may be configured to introduce (e.g., to transport, to deploy, and/or to position) the coil implant in the hollow organ. The microcatheter may have, for example, an inflatable balloon at a distal portion.

By providing the at least one procedure parameter, the embodiment may assist a medical operator in selecting and/or controlling the microcatheter and/or coil implant (e.g., in the course of an embolization).

In a further embodiment of the method for providing at least one procedure parameter, the hollow organ may have an aneurysm and/or a vessel malformation. The at least one procedure parameter may, for example, include a movement specification for inserting the at least one medical object into the aneurysm and/or vessel malformation.

The at least one intraprocedural projection map may map the aneurysm and/or vessel malformation. The at least one procedure parameter may include one or more movement specifications (e.g., a sequence of movement specifications) that specify a movement for the at least one medical object from its instantaneous position, which is mapped in the at least one intraprocedural projection map, into a target position. The target position may, for example, describe a spatial position and/or orientation and/or pose of the at least one medical object in the aneurysm and/or vessel malformation. The target position may describe a spatial position and/or orientation and/or pose of the at least one medical object in the hollow organ during capture of the at least one intraprocedural projection map.

The at least one movement specification may, for example, be specified in absolute or relative terms (e.g., relative to an instantaneous movement of the at least one medical object that is mapped in temporally resolved manner in a plurality of intraprocedural projection maps).

The embodiment may enable improved assistance for a medical operator on insertion of the at least one medical object into an aneurysm and/or a vessel malformation.

In a further embodiment of the method for providing at least one procedure parameter, a preprocedural data set that maps hemodynamics in the hollow organ may be received. The trained function may also be applied in act b) to the preprocedural data set as input data.

The preprocedural data set may include a two-dimensionally (2D) and/or three-dimensionally (3D) spatially resolved map and/or a model of the hemodynamics in the hollow organ of the examination object. The preprocedural data set may map the hemodynamics in the hollow organ of the examination object in temporally resolved manner. The preprocedural data set may be captured within a preprocedural temporal phase (e.g., before capture of the at least one intraprocedural projection map and before positioning of the at least one medical object in the hollow organ of the examination object). The preprocedural data set may map blood flow in the hollow organ (e.g., the aneurysm and/or vessel malformation) in spatially and temporally resolved manner (e.g., via a contrast agent). The preprocedural data set may be captured, for example, via, for example, four-dimensional, digital subtraction angiography (DSA).

In one embodiment, the input data of the trained function may also be based on the preprocedural data set (e.g., include the preprocedural data set).

Since the at least one parameter of the trained function is adjusted based on a simulation of a virtual positioning of at least one medical training object in a training hollow organ and of the hemodynamics in the training hollow organ that are influenced by the at least one medical training object, additionally taking account of the preprocedural data set as input data may enable improved (e.g., more accurate) provision of the at least one procedure parameter.

In a further embodiment of the method for providing at least one procedure parameter, the trained function may include a first neural network and a second neural network. In order to provide a synthetic data set, the first neural network may, for example, be applied to the preprocedural data set and the at least one intraprocedural projection map as input data. The synthetic data set may map simulated hemodynamics in the hollow organ with at least one medical object virtually positioned therein. The second neural network may be applied to the synthetic data set as input data in order to provide the at least one procedure parameter.

The first neural network may be configured to provide the synthetic data set as output data. The first neural network may also be configured to be applied to the preprocedural data set and the at least one intraprocedural projection map (e.g., the plurality of intraprocedural projection maps) as input data. For example, the input data of the first neural network may include the preprocedural data set and the at least one intraprocedural projection map. The second neural network may be configured to provide the at least one procedure parameter as output data. The second neural network may also be configured to be applied to the output data of the first neural network (e.g., to the synthetic data set) as input data. For example, the input data of the second neural network may include the output data of the first neural network.

The synthetic data set may include a two-dimensionally and/or three-dimensionally spatially resolved map and/or a model of simulated hemodynamics in the hollow organ with the at least one medical object virtually positioned therein. In addition, the synthetic data set may be temporally resolved. The synthetic data set may include a plurality of data points (e.g., pixels or voxels) that, in each case, have a time-intensity curve. The simulated hemodynamics in the hollow organ may, for example, be mapped or modeled by temporal intensity changes in the time-intensity curve of the data points. The data points map or model the hollow organ. Alternatively or additionally, the simulated hemodynamics in the hollow organ may be mapped or modeled by values of the data points of the synthetic data set. The values of the data points represent deviations of a variable within the hollow organ (e.g., a gradient) that characterizes the hemodynamics.

The embodiment may enable particularly accurate provision of the at least one procedure parameter (e.g., taking account of an influence of the at least one medical object on the hemodynamics in the hollow organ). For example, a combination of the first neural network and the second neural network may, with the assistance of the input data, construct (e.g., model and/or map) inverse dynamics of a movement (e.g., manipulation) of the at least one medical object.

In a further embodiment of the method for providing at least one procedure parameter, a material parameter and/or an operating parameter regarding the at least one medical object may be received. The input data may, for example, additionally be based on the material parameter and/or operating parameter.

Receiving the material and/or operating parameter of the at least one medical object may include acquiring and/or reading out a computer-readable data memory and/or receiving from a data storage unit (e.g., a database). The material and/or operating parameter may be provided by the at least one medical object. Where the at least one intraprocedural projection map maps the hollow organ with a plurality of medical objects positioned therein, a material and/or operating parameter regarding each medical object of the plurality of medical objects may in each case be received.

The material parameter may include an item of information regarding a geometric characteristic (e.g., a shape and/or diameter, and/or porosity, and/or surface quality, and/or conformability, such as rigidity) of the at least one medical object. The operating parameter may include an item of information regarding an instantaneous operating state of the medical object (e.g., a pose of the medical object, and/or a direction of movement, and/or velocity of movement of the at least one medical object).

In one embodiment, the input data of the trained function may also be based on the material parameter and/or operating parameter. For example, the input data of the trained function may also include the material parameter and/or operating parameter.

In this way, the at least one procedure parameter may also be provided while taking account of the material and/or operating parameter of the at least one medical object.

In a further embodiment of the method for providing at least one procedure parameter, the movement specification may specify a velocity and/or acceleration and/or force for the at least one medical object.

The movement specification may specify the velocity and/or acceleration and/or force for the medical object (e.g., an accelerated or uniform translation and/or rotation of the at least one medical object). The movement specification may, for example, specify the velocity and/or acceleration and/or force with regard to a lengthwise direction of the at least one medical object or of the hollow organ (e.g., along the lengthwise direction or about the lengthwise direction). For example, the movement specification may specify the velocity and/or acceleration and/or force for the at least one medical object in absolute or relative terms (e.g., with regard to a reference point and/or with regard to a movement status (e.g., instantaneous movement status) of the at least one medical object. The force may, for example, be a force acting on a proximal portion of the at least one medical object that effects a translation (e.g., an advance or retraction) and/or a rotation of the least one medical object. The movement specification may include a velocity value and/or an acceleration value and/or a force value. The force may describe an insertion force for inserting the at least one medical object into the aneurysm and/or vessel malformation.

The movement specification may specify the velocity and/or acceleration and/or force for the at least one medical object in absolute or relative terms. According to a first variant, the movement specification may specify the velocity and/or acceleration and/or force for the at least one medical object in absolute terms (e.g., as an absolute velocity value and/or acceleration value and/or force value). Alternatively, the movement specification may specify the velocity and/or acceleration and/or force for the at least one medical object in relative terms (e.g., with respect to an instantaneous movement of the at least one medical object modeled; in temporally resolved manner; in a plurality of intraprocedural projection maps). The movement specification may, for example, specify a modification (e.g., an increase or reduction) of a velocity value and/or acceleration value and/or force value (e.g., instantaneous value).

The embodiment may enable improved assistance for the medical operator in controlling the at least one medical object.

In a further embodiment of the method for providing at least one procedure parameter, acts a) and b) may be carried out repeatedly until a termination condition occurs.

The termination condition may specify a maximum number of repeats of acts a) and b) and/or a maximum duration for repeatedly carrying out acts a) and b). Alternatively or additionally, the termination condition may be specified by an input from a medical operator via an input unit. For example, acts a) and b) may be carried out repeatedly after a predefined period of time. Alternatively or additionally, acts a) and b) may be carried out repeatedly as a function of an object signal. The object signal may, for example, be provided by a sensor for acquiring movement of the at least one medical object. The object signal may include an item of information regarding a movement status of the at least one medical object (e.g., instantaneous movement status). Alternatively or additionally, acts a) and b) may be carried out repeatedly as a function of an input from a medical operator via the input unit.

The embodiment may, for example, adaptively assist the operator during selection and/or control of the at least one medical object. Repeatedly carrying out acts a) and b) may result in repeated provision of the at least one procedure parameter that is advantageously adjusted to the in each case most recently captured at least one intraprocedural projection map.

In a further embodiment of the method for providing at least one procedure parameter, the at least one procedure parameter may be provided to a display unit for displaying a graphical representation of the movement specification. Alternatively or additionally, the at least one procedure parameter may be provided to a movement apparatus for robotic movement of the at least one medical object. The movement apparatus may, for example, be configured to control a movement of the at least one medical object based on the at least one procedure parameter.

The display unit may include a monitor and/or screen and/or projector that is configured to display the graphical representation of the movement specification (e.g., the workflow instruction). For example, the display unit may display the graphical representation of the movement specification at least partially overlaid with a graphical representation of the at least one intraprocedural projection map. The graphical representation of the movement specification may, for example, include a display of the at least one procedure parameter (e.g., of a velocity value and/or acceleration value and/or force value). Alternatively or additionally, the graphical representation of the movement specification may include a display of a specification for modifying (e.g., increasing or reducing) the velocity value and/or acceleration value and/or force value.

In one embodiment, the movement apparatus may be a robotic apparatus that is configured for remote manipulation of the at least one medical object (e.g., a catheter robot). The movement apparatus may be configured to receive (e.g., hold) a proximal portion of the at least one medical object. The movement apparatus may be configured to hold and/or move the at least one medical object by force transfer. For example, the movement apparatus may be configured to arrange and/or move a distal portion of the at least one medical object by force transfer onto the proximal portion.

In one embodiment, provision of the at least one procedure parameter to the movement apparatus may include transfer to the movement apparatus. The movement apparatus may convert the at least one procedure parameter (e.g., the movement specification) into a control parameter for controlling movement of the at least one medical object. The control parameter may, for example, include instructions for controlling the movement apparatus such that the at least one medical object is moved by force transfer from the movement apparatus onto the proximal portion of the medical object according to the at least one procedure parameter (e.g., the movement specification). For example, the movement apparatus may move the at least one medical object according to the specified velocity and/or acceleration and/or force. Movement of the at least one medical object by the movement apparatus according to the at least one procedure parameter (e.g., the movement specification) may proceed after completion of the method for providing the at least one procedure parameter.

Reliable selection and/or control of the medical object by the medical operator may be enabled via the embodiment.

The movement apparatus may acquire and provide the material and/or operating parameter of the at least one medical object (e.g., during capture of the at least one intraprocedural projection map). The movement apparatus may have a sensor that is configured to acquire the material and/or operating parameter (e.g., a mechanical and/or electromagnetic, such as optical, and/or acoustic, such as ultrasound-based, sensor). The movement apparatus (e.g., the sensor) may, for example, acquire the geometric characteristic (e.g., the shape and/or the diameter, and/or the porosity, and/or the surface quality, and/or the conformability, such as the rigidity, and/or the direction of movement, and/or the velocity of movement, and/or the acceleration) of the at least one medical object and provide the geometric characteristic as the material and/or operating parameter. The movement apparatus (e.g., the sensor) may acquire a force acting between the movement apparatus and the at least one medical object and provide a corresponding force value. The input data may, for example, additionally be based on the material parameter and/or operating parameter.

A second aspect of the present embodiments relates to a computer-implemented method for providing a first neural network. A preprocedural training data set that maps hemodynamics in a training hollow organ of a training examination object is, for example, received. A synthetic comparison data set that maps simulated hemodynamics in the training hollow organ with at least one medical training object virtually positioned therein is received. Further, at least one intraprocedural training projection map that maps the training hollow organ with the at least one medical training object positioned therein is received. Alternatively, the at least one intraprocedural training projection map is provided by a virtual projection of the synthetic comparison data set. A synthetic training data set is provided by applying the first neural network to input data that is based on the at least one intraprocedural training projection map and the preprocedural training data set. At least one parameter of the first neural network is then adjusted based on a comparison between the synthetic training data set and the synthetic comparison data set. The first neural network is provided.

Receiving the preprocedural training data set, the synthetic comparison data set, and/or the at least one intraprocedural training projection map may include acquiring and/or reading out a computer-readable data memory and/or receiving from a data storage unit (e.g., a database). The preprocedural training data set may be captured via a medical imaging device. Alternatively, the preprocedural training data set may be simulated. The at least one intraprocedural training projection map may be captured via the same or a further medical imaging device. Alternatively, the at least one intraprocedural training projection map may be provided by a virtual projection (e.g., a virtual forward projection) of the synthetic comparison data set. The virtual projection may include a, for example, realistic simulation that is based on parameters (e.g., actual parameters; capture parameters and/or operating parameters) of the medical imaging device. In one configuration of the medical imaging device as a medical X-ray device (e.g., as a medical C-arm X-ray device and/or computed tomography system), the simulation may include a model (e.g., realistic and/or physical model) of an X-ray source (e.g., an X-ray tube) and/or of an X-ray detector of the medical X-ray device. The simulation may include a model (e.g., a realistic and/or physical and/or biophysical model) of the examination object transilluminated with X-rays and/or physical effects that may occur on transillumination of the examination object and/or on illumination of the X-ray detector with X-rays that are emitted by the medical X-ray device (e.g., the X-ray source). The model of the X-ray source (e.g., of the X-ray tube) may include a probability distribution with regard to an energy and/or direction of emergence of emitted X-ray photons based on an operating parameter of the X-ray source (e.g., an operating voltage and/or filtering and/or age and/or collimation and/or focal spot size). The model of the X-ray detector may include a map of a detection mechanism (e.g., actual detection mechanism) and/or a probability distribution of anticipated noise behavior. Further, a noise power spectrum, modulation transfer function, and/or detective quantum efficiency of the model of the X-ray detector may correspond to the noise power spectrum, modulation transfer function, and/or detective quantum efficiency of the real X-ray detector.

The preprocedural training data set may, for example, include all the characteristics and features of the preprocedural data set that have been described in relation to the method for providing at least one procedure parameter and vice versa. In addition, the at least one intraprocedural training projection map may, for example, include all the characteristics and features of the at least one intraprocedural projection map that have been described in relation to the method for providing at least one procedure parameter and vice versa. Further, the at least one medical training object may, for example, include all the characteristics and features of the at least one medical object that have been described in relation to the method for providing at least one procedure parameter and vice versa.

The training examination object may be a human and/or animal patient and/or an examination phantom. The training examination object may be a simulated patient model. The training hollow organ may have all the features and characteristics of the hollow organ that have been described in relation to the method for providing at least one procedure parameter and vice versa.

The synthetic training data set may be provided by applying the first neural network to the input data. The input data of the first neural network may, for example, be based on the at least one intraprocedural training projection map and the preprocedural training data set. For example, the input data of the first neural network may include the at least one intraprocedural training projection map and the preprocedural training data set. Further, the first neural network may provide the synthetic training data set as output data.

The at least one parameter of the first neural network may be adjusted by comparing the synthetic training data set with the synthetic comparison data set. The comparison between the synthetic training data set and the synthetic comparison data set may include determining a deviation between the synthetic training data set and the synthetic comparison data set (e.g., between data points and/or pixels of the respective data set). The at least one parameter of the first neural network may, for example, be adjusted such that the deviation between the synthetic training data set and the synthetic comparison data set is minimized. Adjustment of the at least one parameter of the first neural network may include optimizing (e.g., minimizing) a cost value of a first cost function, where the first cost function characterizes (e.g., quantifies) the deviation between the synthetic training data set and the synthetic comparison data set. For example, adjustment of the at least one parameter of the first neural network may include a regression of the cost value of the first cost function. The first neural network may, for example, have a U-net architecture with two encoders, where one encoder is configured for receiving the at least one intraprocedural training projection map and a further encoder for receiving the preprocedural training data set.

Providing the first neural network may, for example, include storage on a computer-readable storage medium and/or transfer to a provision unit.

The method may provide a first neural network that may be used in an embodiment of the method for providing at least one procedure parameter and/or a method for providing a trained function.

A third aspect of the present embodiments relates to a computer-implemented method for providing a second neural network. A preprocedural training data set that maps hemodynamics in a training hollow organ of a training examination object is, for example, received. In addition, a synthetic comparison data set is provided as output data of a simulation of a virtual positioning of at least one medical training object in the training hollow organ. The simulation is, for example, based on at least one training procedure parameter that includes a movement specification for the at least one medical training object and the preprocedural training data set as input data. At least one parameter of the second neural network is then adjusted by supervised learning based on the input data and the output data of the simulation. The second neural network is provided.

Receiving the preprocedural training data set may include acquiring and/or reading out a computer-readable data memory and/or receiving from a data storage unit (e.g., a database). The preprocedural training data set may be captured via a medical imaging device. Alternatively, the preprocedural training data set may be simulated. The preprocedural training data set may, for example, include all the characteristics and features of the preprocedural data set that have been described in relation to the method for providing at least one procedure parameter and vice versa.

The synthetic comparison data set may be provided as output data of a simulation of a virtual positioning of the at least one medical training object in the training hollow organ. Simulation of the virtual positioning may include virtually positioning (e.g., arranging) a virtual representation (e.g., a model, such as a skeletonized model or a volume mesh model) of the at least one medical training object in a virtual representation (e.g., a model, such as a center-line model or a volume mesh model) of the training hollow organ. The virtual representation of the training hollow organ may be determined with the assistance of the preprocedural training data set (e.g., additionally with the assistance of the at least one intraprocedural training projection map, such as via segmenting the map of the training hollow organ).

The simulation may be based on one or more training procedure parameters as input data. The at least one training procedure parameter may, for example, be specified with the assistance of a lookup table and/or via an iteration based on an initial training procedure parameter. Alternatively or additionally, the at least one training procedure parameter may be received from a procedure protocol. The training procedure parameter may, for example, include all the features and characteristics of the at least one procedure parameter that have been described in relation to the method for providing at least one procedure parameter and vice versa. The virtual representation of the at least one medical training object may be determined with the assistance of the at least one training procedure parameter. The at least one training procedure parameter may include an item of information (e.g., an identifier) regarding the at least one medical training object.

The simulation may include a deformation of the training hollow organ caused by the virtual positioning of the at least one medical training object in the training hollow organ. In addition, the simulation may include a simulation of the hemodynamics in the training hollow organ that are influenced by the at least one medical training object virtually positioned in the training hollow organ. The simulation may, for example, be based on computational fluid dynamics (CFD). The simulation may be based on the preprocedural training data set as input data.

The second neural network may be configured as a recurrent neural network (RNN). At least one parameter of the second neural network may be adjusted by applying a supervised learning method. The supervised learning may, for example, be based on the input data of the simulation (e.g., the preprocedural training data set) and the output data of the simulation (e.g., the synthetic comparison data set).

The second neural network may be configured to be applied to the synthetic comparison data set as input data and to provide the at least one training procedure parameter as output data.

Providing the second neural network may, for example, include storage on a computer-readable storage medium and/or transfer to a provision unit.

The proposed method may provide a second neural network that may be used in an embodiment of the method for providing at least one procedure parameter and/or a method for providing a trained function.

In a further embodiment of the method for providing a second neural network, a training material parameter and/or a training operating parameter regarding the at least one medical training object may be received. The input data of the simulation may, for example, also be based on the training material parameter and/or training operating parameter.

The training material parameter and the training operating parameter of the medical training object may include all the features and characteristics of the material parameter and operating parameter of the medical object that have been described in relation to the method for providing at least one procedure parameter and vice versa.

Receiving the training material parameter and/or training operating parameter may include acquiring and/or reading out a computer-readable data memory and/or receiving from a data storage unit (e.g., a database). The training material parameter and/or training operating parameter may be provided by the at least one medical training object.

The input data of the simulation may additionally be based on the training material parameter and/or training operating parameter. For example, the input data of the simulation may also include the training material parameter and/or training operating parameter.

In this way, the virtual positioning of the medical training object in the training hollow organ (e.g., an influence on the hemodynamics in the training hollow organ and/or a deformation of the training hollow organ by the at least one medical training object) may be particularly accurately simulated.

A fourth aspect of the present embodiments relates to a computer-implemented method for providing a trained function. A second neural network is, for example, provided by carrying out a method for providing a second neural network. A first neural network is provided by carrying out a method for providing a first neural network. In addition, the trained function including the first neural network and the second neural networks is provided. The trained function is, for example, configured to be applied to the preprocedural training data set and the at least one intraprocedural training projection map as input data and to provide the at least one training procedure parameter as output data.

In one embodiment, a second neural network (e.g., trained second neural network) with at least one adjusted parameter may be provided by carrying out a method for providing a second neural network. The synthetic comparison data set, which is provided as the output data of the simulation, may, for example, be provided for carrying out the method for providing the first neural network. Further, a first neural network (e.g., trained neural network) with at least one adjusted parameter may be provided by carrying out a method for providing a first neural network. The trained function including the first neural network and the second neural networks may, for example, be provided. For example, the output layer of the first neural network may be linked with an input layer of the second neural network. In this way, the output data of the first neural network (e.g., the synthetic training data set) may be provided as input data to the second neural network. In this way, the trained function may be configured to be applied to the preprocedural training data set and the at least one intraprocedural training projection map as input data. For example, the input data of the trained function may include the preprocedural training data set and the at least one intraprocedural training projection map. The trained function may further be configured to provide the at least one training procedure parameter as output data. For example, the output data of the trained function may include the at least one training procedure parameter.

Via the embodiment, a trained function that is configured to process the at least one intraprocedural projection map (e.g., the at least one intraprocedural training projection map) may be provided as input data, and the at least one procedure parameter (e.g., the at least one training procedure parameter) may be provided as output data. The hemodynamics influenced by the at least one medical object (e.g., the at least one medical training object) are taken into account. The method may provide a trained function that may be used in an embodiment of the method for providing at least one procedure parameter.

A fifth aspect of the present embodiments relates to a further computer-implemented method for providing a trained function. Input data is, for example, received, where the input data includes at least one intraprocedural training projection map that maps a training hollow organ with at least one medical training object positioned therein. Alternatively, the input data includes a synthetic training data set that maps simulated hemodynamics in the training hollow organ with at least one medical training object virtually positioned therein. The at least one intraprocedural training projection map is, for example, provided by a virtual projection of the synthetic training data set. Further, at least one parameter of the trained function is adjusted via reinforcement learning such that a reward value is maximized. Adjustment of the at least one parameter of the trained function includes providing at least one training procedure parameter, simulating a virtual positioning of the at least one medical training object in the training hollow organ based on the at least one training procedure parameter and the input data, and simulating hemodynamics in the training hollow organ that are influenced by the at least one medical training object in the virtual position and determining the reward value. Determination of the reward value is, for example, based on a packing density of the at least one medical training object in the training hollow organ, a probability of rupture of the training hollow organ by the at least one medical training object, and/or occlusion of the training hollow organ by the at least one medical training object. The trained function is configured to provide the at least one training procedure parameter having the maximum reward value as output data by adjustment of the at least one parameter. The trained function is provided.

Receiving the input data (e.g., the at least one intraprocedural training projection map or the synthetic training data set) may include acquiring and/or reading out a computer-readable data memory and/or receiving from a data storage unit (e.g., a database). The at least one intraprocedural training projection map may be captured via a medical imaging device. Alternatively, the at least one intraprocedural training projection map may be provided by a virtual projection of the synthetic training data set.

The at least one intraprocedural training projection map may, for example, include all the features and characteristics of the at least one intraprocedural projection map that have been described in relation to the method for providing at least one procedure parameter and vice versa. In addition, the synthetic training data set may include all the features and characteristics of the synthetic data set that have been described in relation to the method for providing a procedure parameter and vice versa.

Adjustment of the at least one parameter of the trained function may include application of a reinforcement learning method. The trained function may, for example, be configured as a recurrent neural network (RNN). The reinforcement learning method for adjusting the at least one parameter of the trained function may include a plurality of steps that are carried out repeatedly (e.g., iteratively). In a first act, at least one training procedure parameter may be provided. The at least one training procedure parameter may, for example, include all the features and characteristics of the at least one procedure parameter that have been described in relation to the method for providing at least one procedure parameter and vice versa. The at least one training procedure parameter may, for example, be specified with the assistance of a lookup table and/or by way of an iteration on the basis of an initial training procedure parameter. Alternatively or additionally, the at least one training procedure parameter may be received from a procedure protocol.

In a further act, the virtual positioning of the at least one medical training object in the training hollow organ may be simulated based on the at least one training procedure parameter and the input data (e.g., the at least one intraprocedural training projection map). Simulation of the virtual positioning may include virtually positioning (e.g., arranging) a virtual representation (e.g., a model, such as a skeletonized model or a volume mesh model) of the at least one medical training object in a virtual representation (e.g., a model, such as a center-line model or a volume mesh model) of the training hollow organ. The virtual representation of the training hollow organ may be determined with the assistance of the at least one intraprocedural training projection map and/or with the assistance of the synthetic training data set (e.g., via segmenting the map of the training hollow organ). The virtual representation of the at least one medical training object may be determined with the assistance of the at least one training procedure parameter and/or with the assistance of the at least one intraprocedural training projection map (e.g., via segmenting the map of the at least one medical training object in the at least one intraprocedural training projection map). The at least one training procedure parameter may include an item of information (e.g., an identifier) regarding the at least one medical training object. The simulation may include a mechanical interaction with the training hollow organ (e.g., deformation of the training hollow organ) caused by the virtual positioning of the at least one medical training object in the training hollow organ.

In addition, hemodynamics in the training hollow organ that are influenced by the at least one medical training object in the virtual position may be simulated. The simulation may, for example, be based on computational fluid dynamics (CFD). The simulation may include providing virtual image data (e.g., virtual projection maps, such as virtual X-ray projection maps).

In a further act, the reward value may be determined based on a packing density of the at least one medical training object in the hollow organ and a probability of rupture and/or occlusion of the training hollow organ by the at least one medical training object virtually positioned therein. The packing density may describe a ratio of a volume of the at least one medical training object to a volume of the training hollow organ. The packing density may, for example, be normalized. The packing density may provide a measure of the occlusion of the training hollow organ (e.g., of the aneurysm and/or vessel malformation) with the at least one medical training object virtually positioned therein. An optimum packing density for occluding the aneurysm and/or vessel malformation may be achieved at a ratio of the volumes of the at least one medical training object to the training hollow organ (e.g., aneurysm and/or vessel malformation) of 1. The reward value may be determined proportionally to the packing density up to the optimum value of 1.

Rupture of the training hollow organ may be brought about by direct mechanical action of the at least one medical training object on the training hollow organ and/or by overpacking of the training hollow organ with the at least one medical training object. At a ratio of the volumes of the at least one medical training object to the training hollow organ of greater than 1, there may be a risk of rupture of the training hollow organ (e.g., of the aneurysm and/or vessel malformation). The probability of rupture of the training hollow organ by the at least one medical training object may be determined with the assistance of a simulated (e.g., mechanical) interaction between the at least one medical training object in the virtual position and the training hollow organ. The probability of rupture may thus be determined with the assistance of the packing density of the at least one medical training object in the training hollow organ and/or with the assistance of the simulated interaction between the at least one medical training object in the virtual position and the training hollow organ. The probability of occlusion (e.g., arterial occlusion) by the at least one medical training object virtually positioned in the training hollow organ may be determined. The probability of occlusion (e.g., arterial occlusion) of the training hollow organ may, for example, be determined based on a modification of the simulated hemodynamics in the training hollow organ that are influenced by the at least one medical training object virtually positioned in the training hollow organ. For example, a probability of a thromboembolic event brought about by the at least one medical training object in the virtual position may be determined with the assistance of the simulated hemodynamics in the training hollow organ.

The reward value may be determined such that a high reward value is determined for a low probability of rupture and/or occlusion of the training hollow organ by the at least one medical training object.

During supervised learning, an agent (e.g., a learning agent) may be used for determination (e.g., iterative determination) of the reward value. The agent may, for example, be based on a neural network or a lookup table (e.g., a Q-table). The agent may be configured to receive an initial state of the training examination object (e.g., of the training hollow organ). The initial state may, for example, be specified with the assistance of the at least one intraprocedural training map. By adjusting the at least one parameter of the trained function, the agent may determine the at least one training procedure parameter that maximizes the reward value. In this way, the trained function may be configured, on application to the input data, to provide the at least one training procedure parameter with the maximum reward value as output data.

Providing the trained function may, for example, include storage on a computer-readable storage medium and/or transfer to a provision unit.

The method may provide a trained function that may be used in an embodiment of the method for providing at least one procedure parameter.

In a further embodiment of the further method for providing a trained function, a preprocedural training data set that maps hemodynamics in the training hollow organ of the training examination object may be received. The input data of the trained function may, for example, additionally be based on the preprocedural training data set.

Receiving the preprocedural training data set may include acquiring and/or reading out a computer-readable data memory and/or receiving from a data storage unit (e.g., a database). The preprocedural training data set may be captured via a medical imaging device. Alternatively, the preprocedural training data set may be simulated.

The preprocedural training data set may, for example, include all the features and characteristics of the preprocedural data set that have been described in relation to the method for providing at least one procedure parameter and vice versa.

In one embodiment, the input data of the trained function may additionally be based on the preprocedural training data set. For example, the input data of the trained function may also include the preprocedural training data set.

For example, the input data of the simulation of the hemodynamics in the training hollow organ that are influenced by the at least one medical training object may additionally be based on the preprocedural training data set. The virtual representation of the training hollow organ may, for example, additionally be determined with the assistance of the preprocedural training data (e.g., via segmenting the map of the training hollow organ in the preprocedural training data set). The simulation may comprise adjustment of the hemodynamics (e.g., uninfluenced hemodynamics) in the training hollow organ in the preprocedural training data set to the virtual position of the at least one medical training object. In this way, improved (e.g., more accurate) provision of the at least one training procedure parameter may be enabled by applying the trained function to the input data.

A sixth aspect of the present embodiments relates to a system including an imaging unit and a provision unit. The system is, for example, configured to carry out a method for providing at least one procedure parameter. In addition, the imaging unit is configured to capture the at least one intraprocedural projection map and provide the at least one intraprocedural projection map to the provision unit. The provision unit is configured to provide the at least one procedure parameter.

The advantages of the system substantially correspond to the advantages of the method for providing at least one procedure parameter. Features, advantages, or alternative embodiments mentioned in this connection are likewise also applicable to the other claimed subject matter and vice versa.

The imaging unit may take the form of a medical X-ray device (e.g., medical C-arm X-ray device) and/or computed tomography system (CT system).

In a further embodiment of a system, the system may also include a display unit and/or a movement apparatus for robotic movement of the at least one medical object. The provision unit may, for example, be configured to provide the at least one procedure parameter to the display unit and/or the movement apparatus.

The display unit may be configured to display a graphical representation of the movement specification.

The movement apparatus may, for example, take the form of a catheter robot (e.g., for remote manipulation of the at least one medical object). In an operating state of the system, the at least one medical object may be positioned at least in part in the hollow organ of the examination object. The movement apparatus may be configured to hold and/or move the at least one medical object by force transfer. The movement apparatus may, for example, be configured to move the at least one medical object positioned therein translationally at least along a lengthwise direction of the medical object. The movement apparatus may be configured to rotate the at least one medical instrument about the lengthwise direction. Alternatively or additionally, the movement apparatus may be configured to control a movement of at least part of the at least one medical object (e.g., a distal portion of the at least one medical object). The movement apparatus may be configured to deform the at least one medical object (e.g., the distal portion) in defined manner (e.g., via a Bowden cable within the at least one medical object).

The movement apparatus may have a sensor that is configured to acquire and provide a material and/or operating parameter of the at least one medical object.

The provision unit may be configured to provide the at least one procedure parameter to the movement apparatus (e.g., via a signal). The movement apparatus may be configured to move the at least one medical object based on the at least one procedure parameter.

A seventh aspect of the present embodiments relates to a training unit that is configured to carry out a computer-implemented method for providing a first neural network, a proposed computer-implemented method for providing a second neural network, a proposed computer-implemented method for providing a trained function, and/or a further computer-implemented method for providing a trained function.

The training unit can include a training interface, a training memory unit, and/or a training computing unit. The training unit may be configured to carry out a method for providing a trained function, a method for providing a first neural network, a method for providing a second neural network and/or a further method for providing a trained function by the training interface, the training memory unit, and/or the training computing unit being configured to carry out the corresponding method acts.

The advantages of the training unit substantially correspond to the advantages of the method for providing a trained function, of the method for providing a first neural network, of the method for providing a second neural network, and/or of the further method for providing a trained function. Features, advantages, or alternative embodiments mentioned in this connection are likewise also applicable to the other subject matter and vice versa.

An eighth aspect of the present embodiments relates to a computer program product with a computer program that may be directly loaded into a memory of a provision unit, having program parts for carrying out all the acts of the method for providing at least one procedure parameter and/or one of the aspects thereof, when the program parts are run by the provision unit. Alternatively or additionally, the computer program may be directly loaded into a training memory of a training unit, having program parts for carrying out all the acts of a method for providing a trained function, of a method for providing a first neural network, of a method for providing a second neural network, and/or of a further method for providing a trained function, and/or the respective aspects thereof when the program parts are run by the training unit.

The present embodiments may also relate to a computer program or computer-readable storage medium (e.g., a non-transitory computer-readable storage medium) including a trained function provided by a proposed computer-implemented method or one of the aspects thereof.

A largely software-based embodiment has the advantage that provision units and/or training units that are already in service may also straightforwardly be retrofitted to operate in the manner according to the present embodiments by a software update. In addition to the computer program, such a computer program product may optionally include additional elements such as, for example, documentation and/or additional components, as well as hardware components, such as, for example, hardware keys (e.g., dongles, etc.) for using the software.

BRIEF DESCRIPTION OF THE DRAWINGS

Embodiments of the invention are shown in the drawings and described in greater detail below. Same reference characters are used for same features in different figures. In the figures.

DETAILED DESCRIPTION

Figure 1:
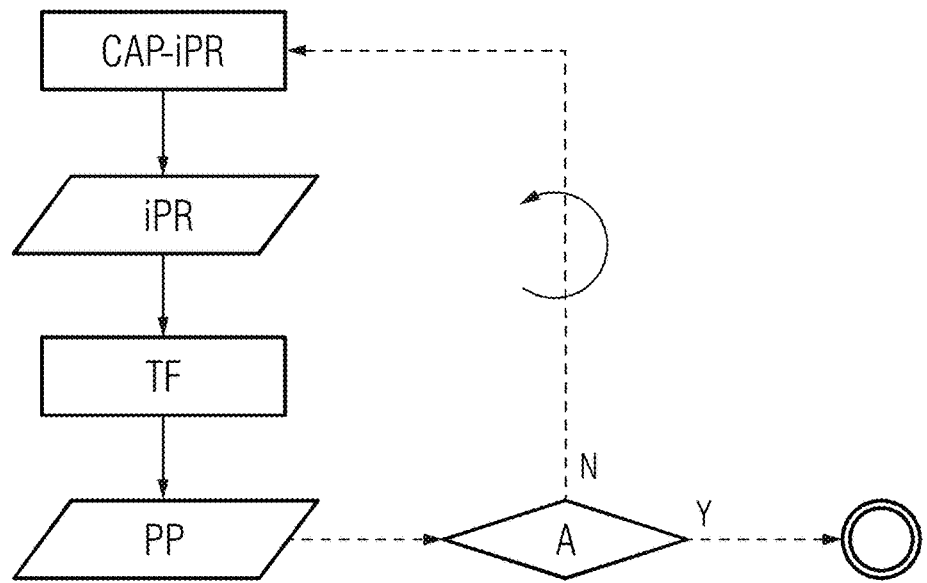
FIGS. 1 to 3 show schematic representations of embodiments of a method for providing at least one procedure parameter.

FIG. 1 is a schematic representation of an embodiment of a method for providing PROV-PP at least one procedure parameter PP. In act a), at least one intraprocedural projection map iPR may be acquired CAP-iPR. The at least one intraprocedural projection map iPR maps a hollow organ of an examination object with at least one medical object positioned in the hollow organ. In act b), a trained function TF may be applied to the at least one intraprocedural projection map iPR as input data. At least one parameter of the trained function TF may, for example, be adjusted based on a simulation of a virtual positioning of at least one medical training object in a training hollow organ and of the hemodynamics in the training hollow organ, which are influenced by the at least one medical training object. Further, the at least one procedure parameter PP may be provided as output data of the trained function PF. The at least one procedure parameter PP may include a movement specification for the at least one medical object. The movement specification may specify a velocity and/or acceleration and/or force for the at least one medical object.

The at least one medical object may, for example, include a microcatheter and/or a coil implant. The at least one intraprocedural projection map iPR may map a plurality of medical objects that are positioned in the hollow organ. The least one procedure parameter PP may include a movement specification for the plurality of medical objects. The hollow organ may have an aneurysm and/or a vessel malformation. The at least one procedure parameter PP may, for example, include a movement specification for inserting the at least one medical object into the aneurysm and/or vessel malformation.

Acts a) and b) may be carried out repeatedly until a termination condition A occurs Y.

Figure 2:
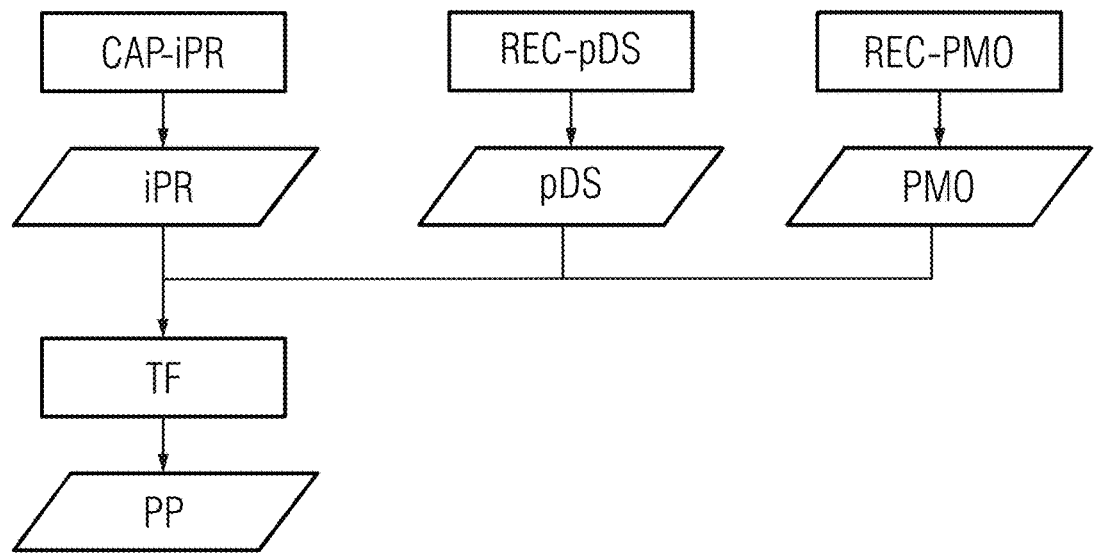

FIG. 2 is a schematic representation of an embodiment of a method for providing PROV-PP at least one procedure parameter PP. A preprocedural data set pDS that maps hemodynamics in the hollow organ may, for example, be received REC-pDS. The trained function TF may additionally be applied in act b) to the preoperative data set pDS as input data.

A material and/or operating parameter PMO regarding the at least one medical object may be received REC-PMO. The input data of the trained function TF may, for example, additionally be based on the material and/or operating parameter PMO.

Figure 3:
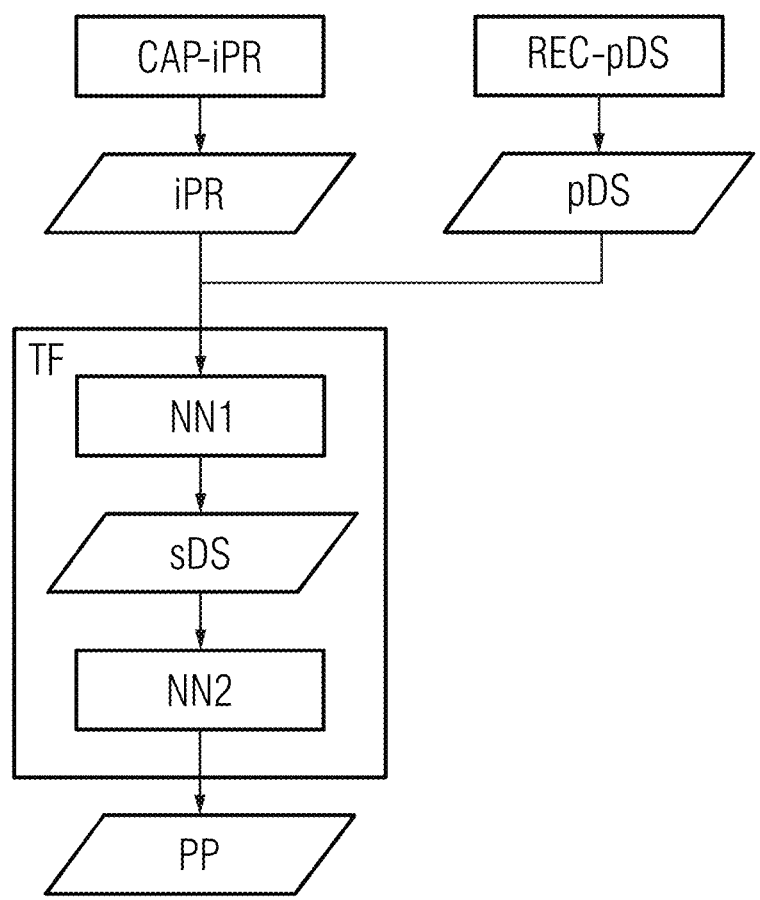

FIG. 3 is a schematic representation of an embodiment of a method for providing PROV-PP at least one procedure parameter PP. The trained function TF may, for example, include a first neural network NN1 and a second neural network NN2. In order to provide a synthetic data set sDS, the first neural network NN1 may be applied to the preprocedural data set pDS and the at least one intraprocedural projection map iPR as input data. The synthetic data set may, for example, map simulated hemodynamics in the hollow organ with at least one medical object virtually positioned therein. In order to provide PROV-PP the at least one procedure parameter PP, the second neural network NN2 may be applied to the synthetic data set sDS as input data.

Figure 4:
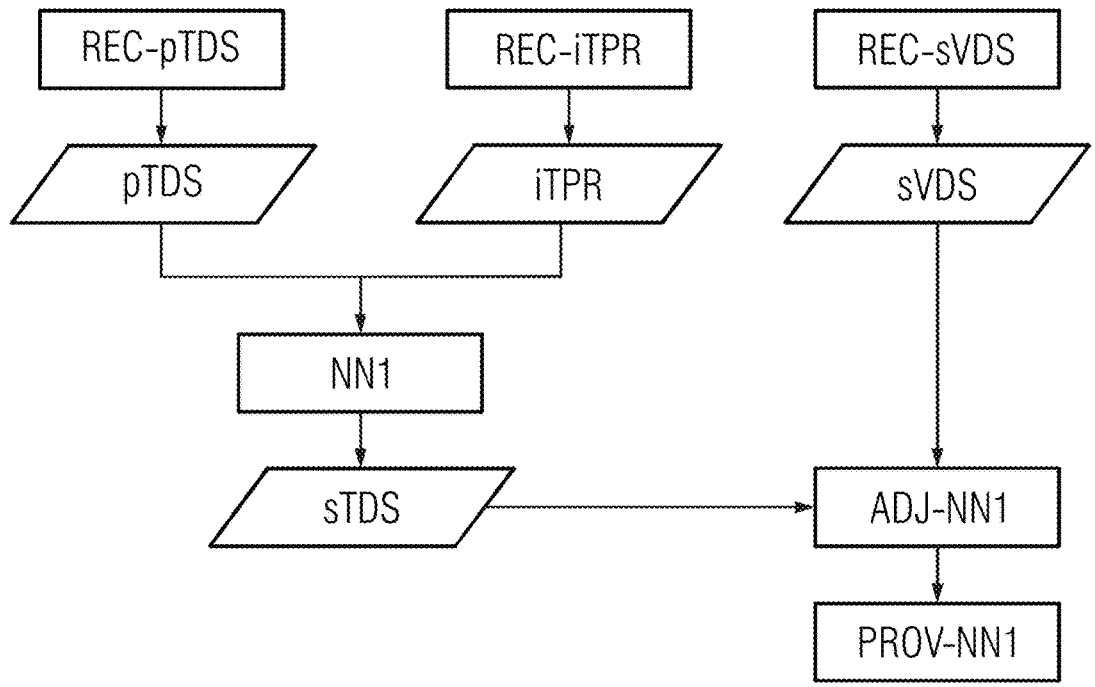
FIGS. 4 and 5 show schematic representations of embodiments of a computer-implemented method for providing a first neural network.

FIG. 4 is a schematic representation of an embodiment of a computer-implemented method for providing PROV-NN1 a first neural network NN1. A preprocedural training data set pTDS that maps hemodynamics in a training hollow organ of an examination object may, for example, be received REC-pTDS. A synthetic comparison data set sVDS that maps simulated hemodynamics in the training hollow organ with at least one medical training object virtually positioned therein may be received REC-sVDS. In addition, at least one intraprocedural training projection map iTPR that maps the training hollow organ with the at least one medical training object positioned therein may be received REC-iTPR. A synthetic training data set sTDS may be provided by applying the first neural network NN1 to input data that is based on the at least one intraprocedural training projection map iTPR and the preprocedural training data set pTDS. At least one parameter of the first neural network NN1 may, for example, be adjusted ADJ-NN1 based on a comparison between the synthetic training data set sTDS and the synthetic comparison data set sVDS. The first neural network NN1 may then be provided PROV-NN1.

Figure 5:
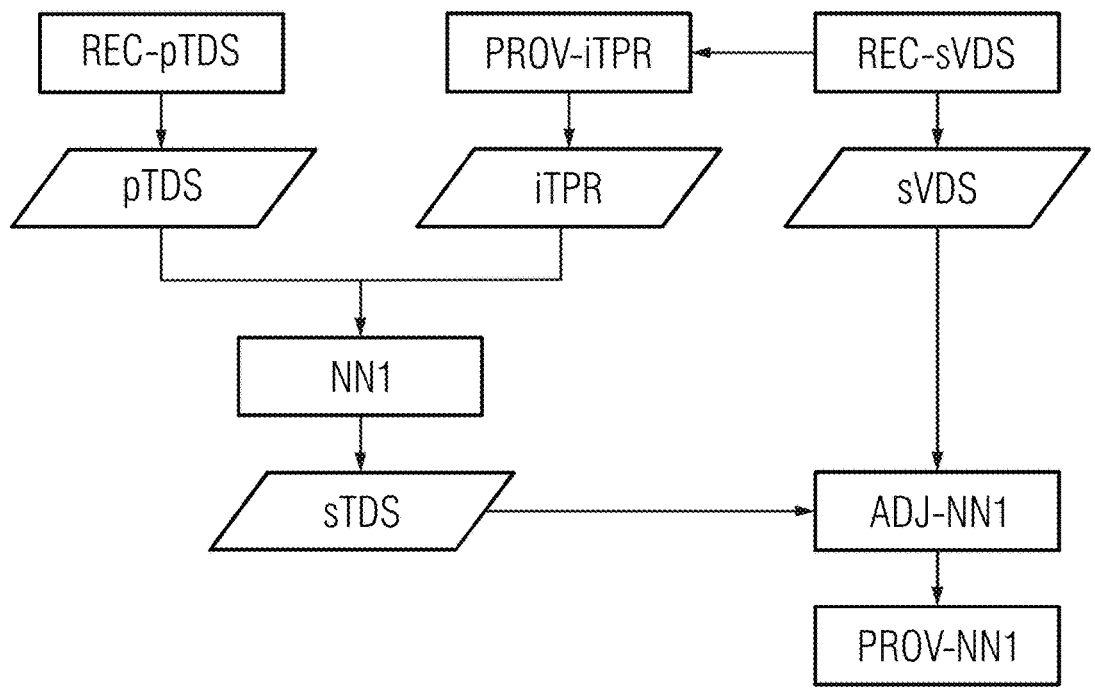

FIG. 5 is a schematic representation of an embodiment of a computer-implemented method for providing PROV-NN1 a first neural network NN1. The at least one intraprocedural training projection map iTPR may, for example, be provided PROV-iTPR by a virtual projection of the synthetic comparison data set sVDS.

Figure 6:
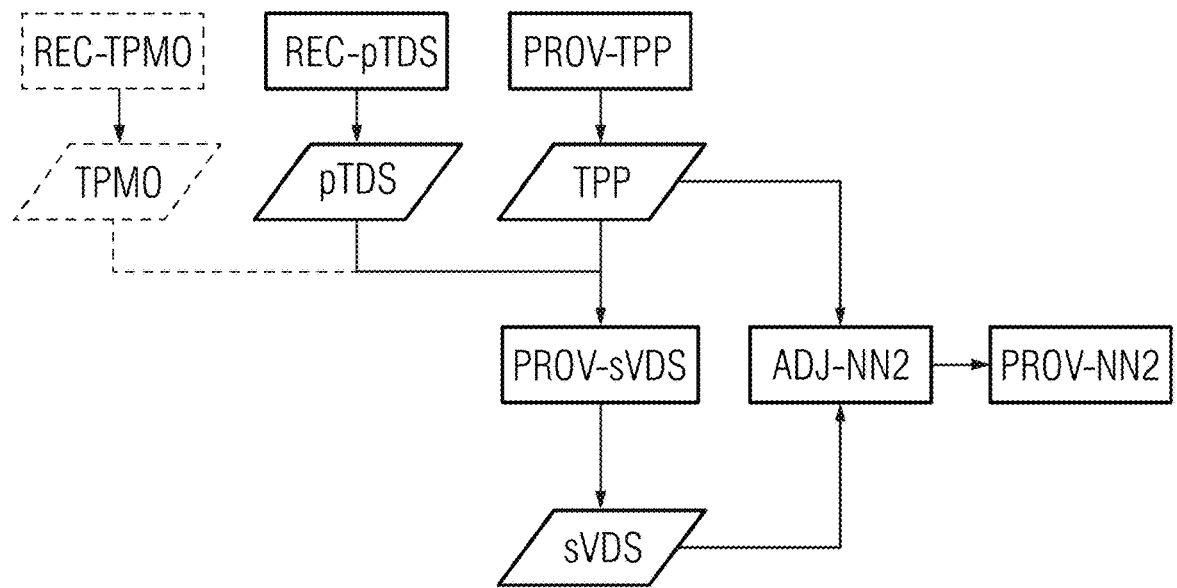
FIG. 6 shows a schematic representation of an embodiment of a computer-implemented method for providing a second neural network.

FIG. 6 is a schematic representation of an embodiment of a computer-implemented method for providing PROV-NN2 a second neural network NN2. A preprocedural training data set pTDS that maps hemodynamics in a training hollow organ of a training examination object may, for example, be received REC-pTDS. A synthetic comparison data set sVDS may be provided PROV-sVDS as output data of a simulation of a virtual positioning of at least one medical training object in the training hollow organ. The simulation may, for example, be based on at least one training procedure parameter TPP that includes a movement specification for the at least one medical training object, and the preprocedural training data set pTDS as input data. The at least one training procedure parameter TPP may, for example, be specified PROV-TPP with the assistance of a lookup table and/or via an iteration based on an initial training procedure parameter. Alternatively or additionally, the at least one training procedure parameter TPP may be received PROV-TPP from a procedure protocol.

At least one parameter of the second neural network NN2 may be adjusted ADJ-NN2 by supervised learning based on the input data and the output data of the simulation. The second neural network NN2 may then be provided PROV-NN2.

A training material parameter and/or training operating parameter TPMO regarding the at least one medical training object may be received REC-TPMO. The input data of the simulation may, for example, additionally be based on the training material parameter and/or training operating parameter TPMO.

Figure 7:
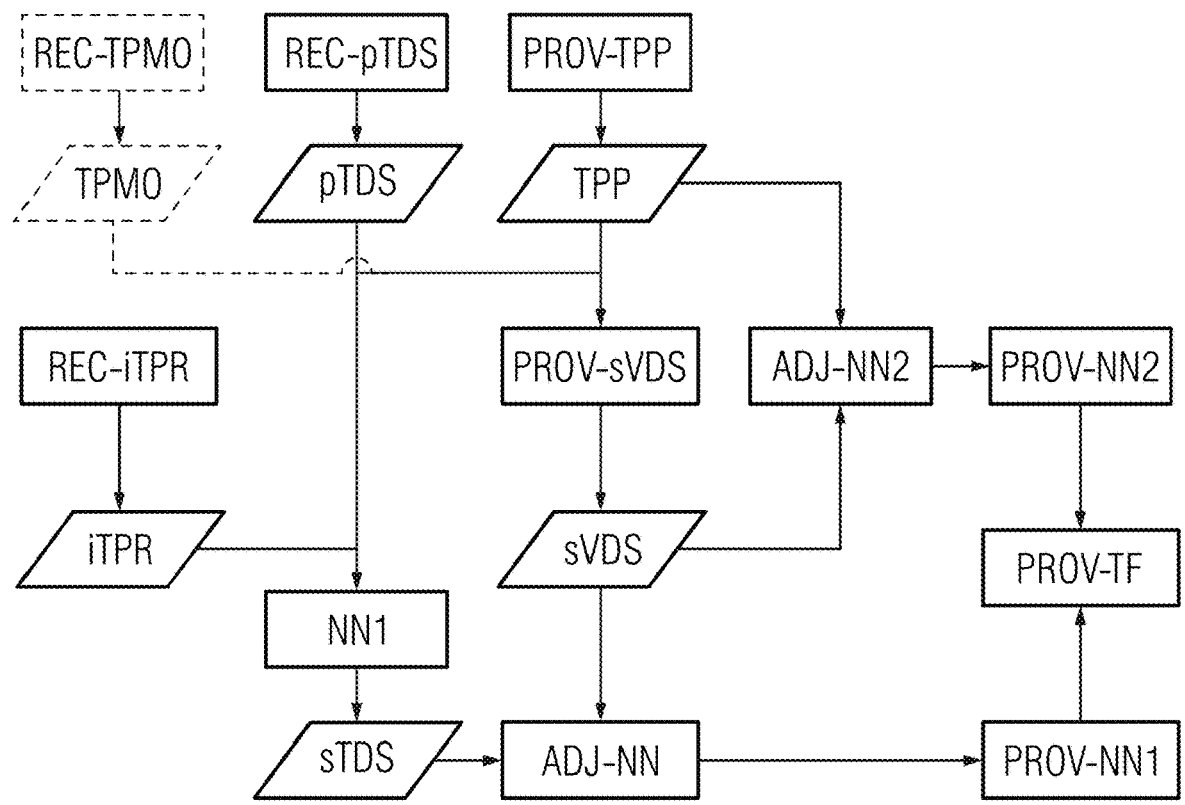
FIG. 7 shows a schematic representation of an embodiment of a computer-implemented method for providing a trained function.

FIG. 7 is a schematic representation of an embodiment of a computer-implemented method for providing PROV-TF a trained function TF. A second neural network NN2 may, for example, be provided PROV-NN2 by carrying out a computer-implemented method for providing PROV-NN2 a second neural network NN2. A first neural network NN1 may be provided by carrying out a proposed computer-implemented method for providing PROV-NN1 a first neural network NN1. The trained function TF including the first neural network NN1 and the second NN2 neural network may, for example, be provided PROV-TR. The trained function TF may be configured to be applied to the preprocedural training data set pTDS and the at least one intraprocedural training projection map iTPR as input data. In addition, the trained function TF may be configured to provide the at least one training procedure parameter TPP as output data.

Figure 8:
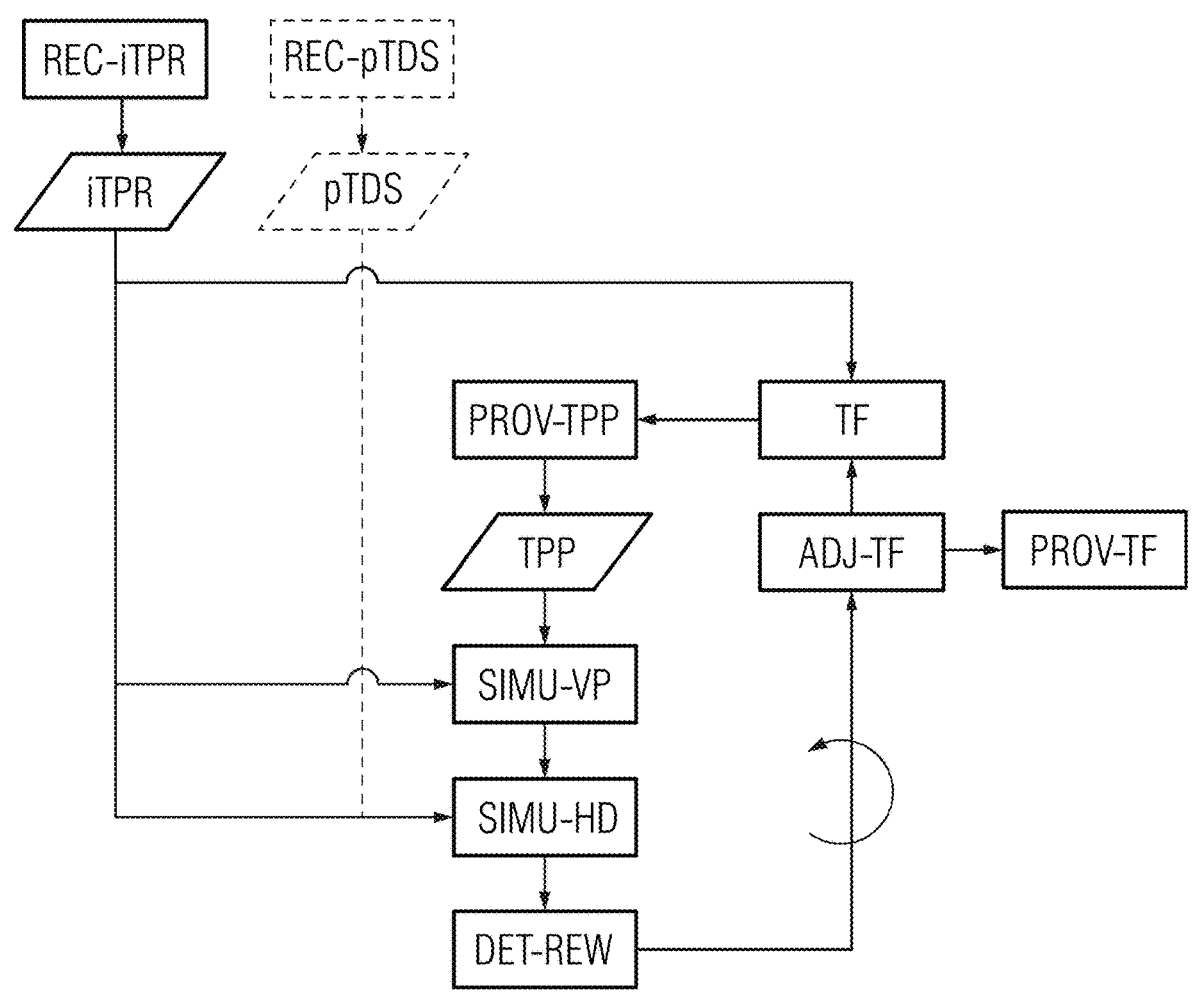
FIGS. 8 and 9 show schematic representations of embodiments of a further computer-implemented method for providing a trained function.

FIG. 8 is a schematic representation of a further computer-implemented method for providing PROV-TF a trained function TF. Input data that includes at least one intraprocedural training projection map iTPR may, for example, be received. The at least one intraprocedural training projection map iTPR may map a training hollow organ with at least one medical training object positioned therein. At least one parameter of the trained function may be adjusted ADJ-TF via reinforcement learning such that a reward value is maximized. Adjustment ADJ-TF of the at least one parameter of the trained function may include a plurality of acts. In a first act, at least one training procedure parameter TPP may be provided PROV-TPP. In a further act, virtual positioning of the at least one medical training object in the training hollow organ may be simulated SIMU-VP based on the training procedure parameter and the input data. Hemodynamics in the training hollow organ that are influenced by the at least one medical training object in the virtual position may be simulated SIMV-HD. In addition, the reward value may be determined DET-REW based on a packing density of the at least one medical training object in the training hollow organ, a probability of rupture of the training hollow organ by the at least one medical training object, and/or a probability of occlusion of the training hollow organ by the at least one medical training object. The trained function TF may be configured to provide the at least one training procedure parameter TPP having the maximum reward value as output data by adjustment ADJ-TF of the at least one parameter. The trained function TF may then be provided PROV-TF.

In one embodiment, a preprocedural training data set pTDS that maps hemodynamics in the training hollow organ of the training examination object may additionally be received REC-pTDS. The input data of the trained function TF may, for example, additionally be based on the preprocedural training data set pTDS.

Figure 9:
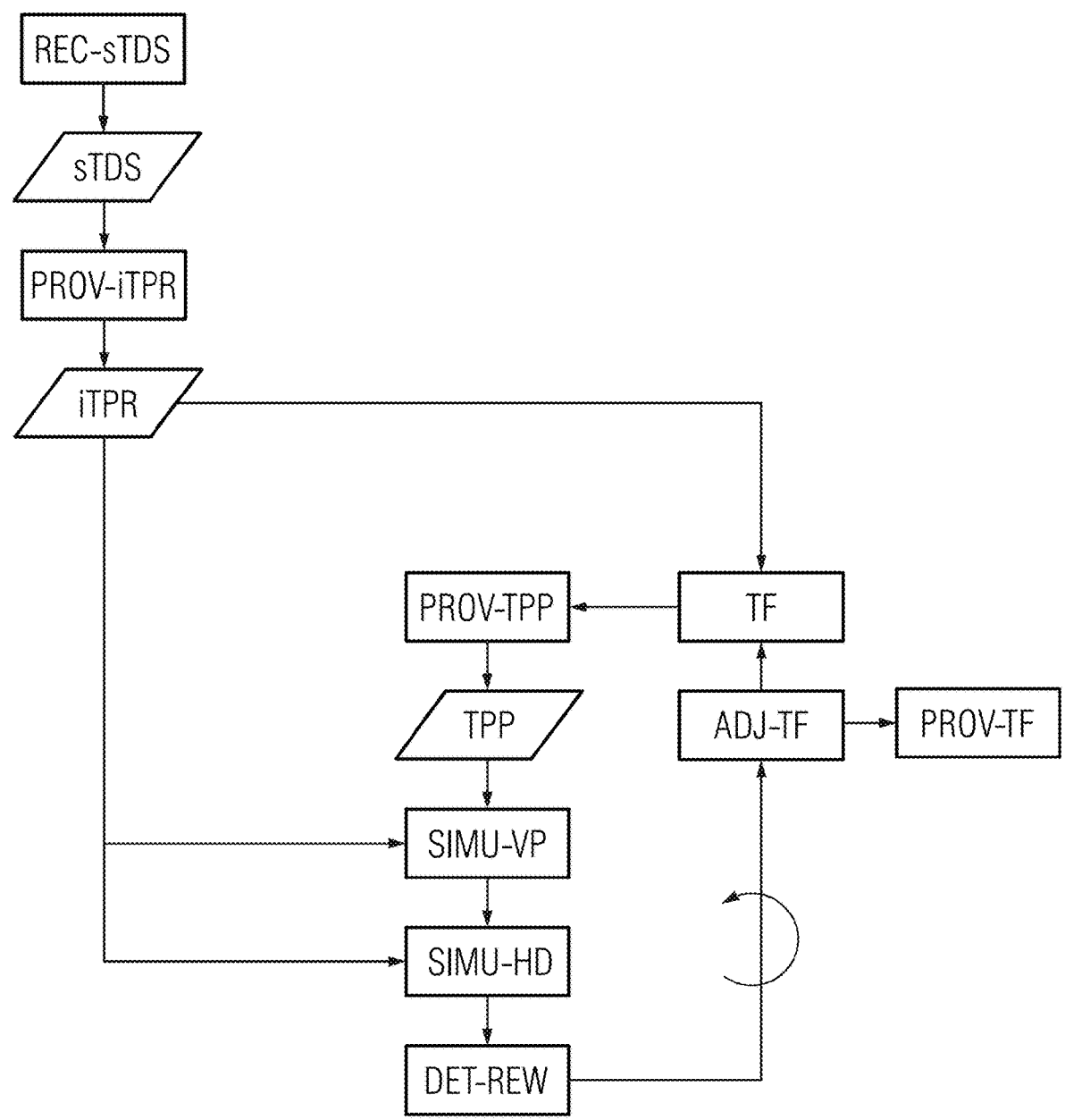

FIG. 9 is a schematic representation of a further embodiment of the further computer-implemented method for providing PROV-TF a trained function TF. The input data including a synthetic training data set sTDS that maps simulated hemodynamics in the training hollow organ with at least one medical training object positioned therein may, for example, be received REC-sTDS. The at least one intraprocedural training projection map iTPR may be provided PROV-iTPR by a virtual projection of the synthetic training data set sTDS.

Figure 10:
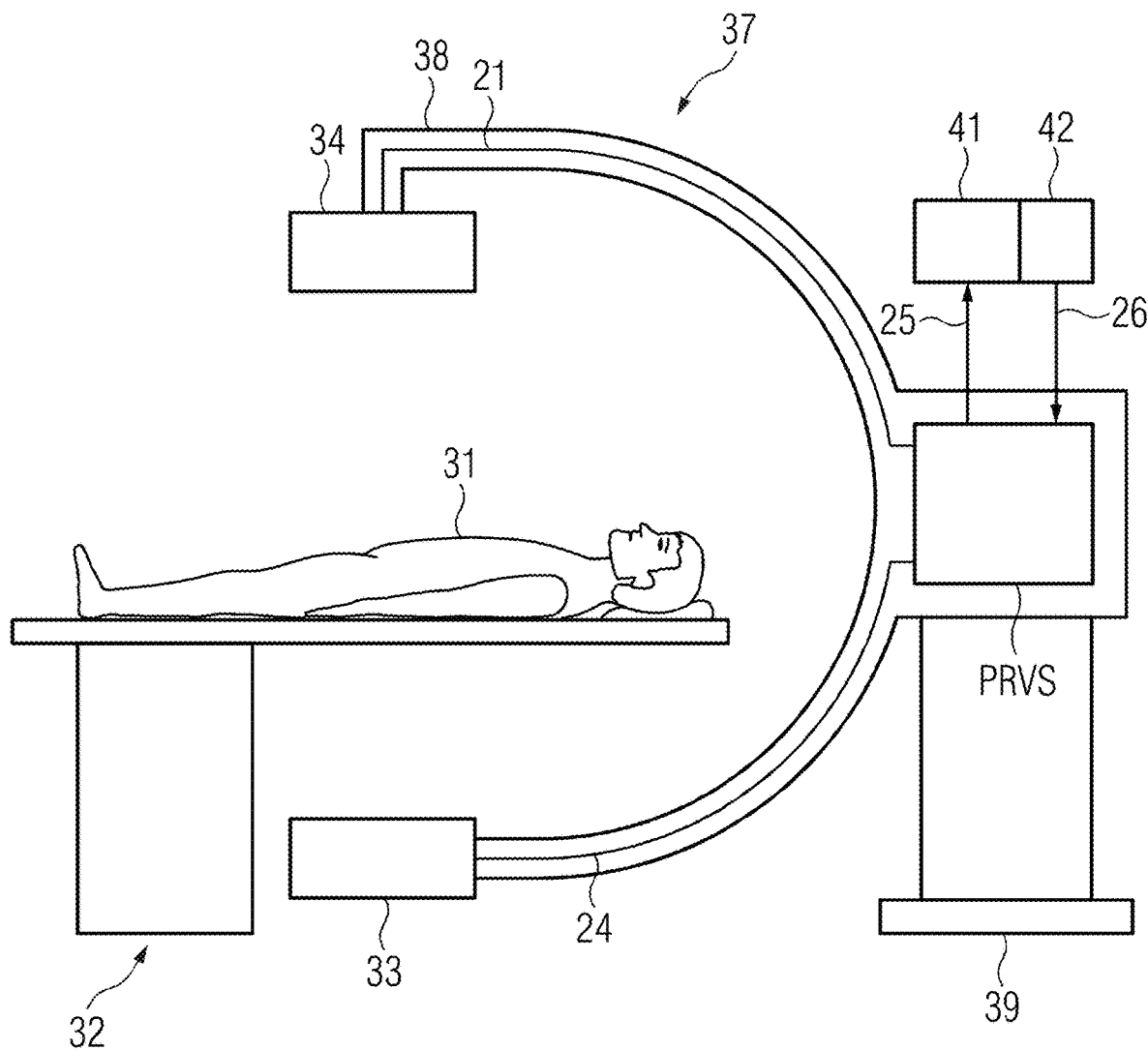
FIGS. 10 and 11 show schematic representations of embodiments of a system.

FIG. 10 is a schematic representation of an embodiment of a proposed system. The system may, for example, include an imaging unit and a provision unit PRVS. The imaging unit may, for example, take the form of a medical C-arm X-ray device 37. The system may be configured to carry out a method of the present embodiments for providing PROV-PP at least one procedure parameter PP. The imaging unit (e.g., the medical C-arm X-ray device 37) may, for example, be configured to capture the at least one intraprocedural projection map iPR and provide the at least one intraprocedural projection map iPR to the provision unit PRVS. The medical C-arm X-ray device 37 may include a detector 34 (e.g., an X-ray detector) and a source 33 (e.g., an X-ray source). In order to capture the at least one intraprocedural projection map iPR, a C-arm 38 of the C-arm X-ray device 37 may be mounted in mobile manner about one or more axes. The medical C-arm X-ray device 37 may include a movement unit 39 that is configured to move the medical C-arm X-ray device 37 spatially.

In order to capture the at least one intraprocedural projection map iPR of the examination object 31 positioned on a patient positioning apparatus 32, the provision unit PRVS may send a signal 24 to the X-ray source 33. Thereupon, the X-ray source 33 may emit an X-ray beam. When, after interacting with the examination object 31, the X-ray beam impinges on a surface of the detector 34, the detector 34 may send a signal 21 to the provision unit PRVS. The provision unit PRVS may, with the assistance of the signal 21, receive the at least one intraprocedural projection map iPR.

The provision unit PRVS may be configured to provide PROV-PP the at least one procedure parameter PP by applying the trained function to the at least one intraprocedural projection map iPR as input data.

The system may also have an input unit 42 (e.g., a keyboard) and a display unit 41 (e.g., a monitor and/or a display and/or a projector). The input unit 42 (e.g., in the case of a capacitive and/or resistive input display) may be integrated in the display unit 41. The input unit 42 may be configured for acquiring user input. To this end, the input unit 42 may, for example, send a signal 26 to the provision unit PRVS.

The display unit 41 may be configured to display a graphical representation of the at least one procedure parameter. The provision unit PRVS may send a signal 25 to the display unit 41.

Figure 11:
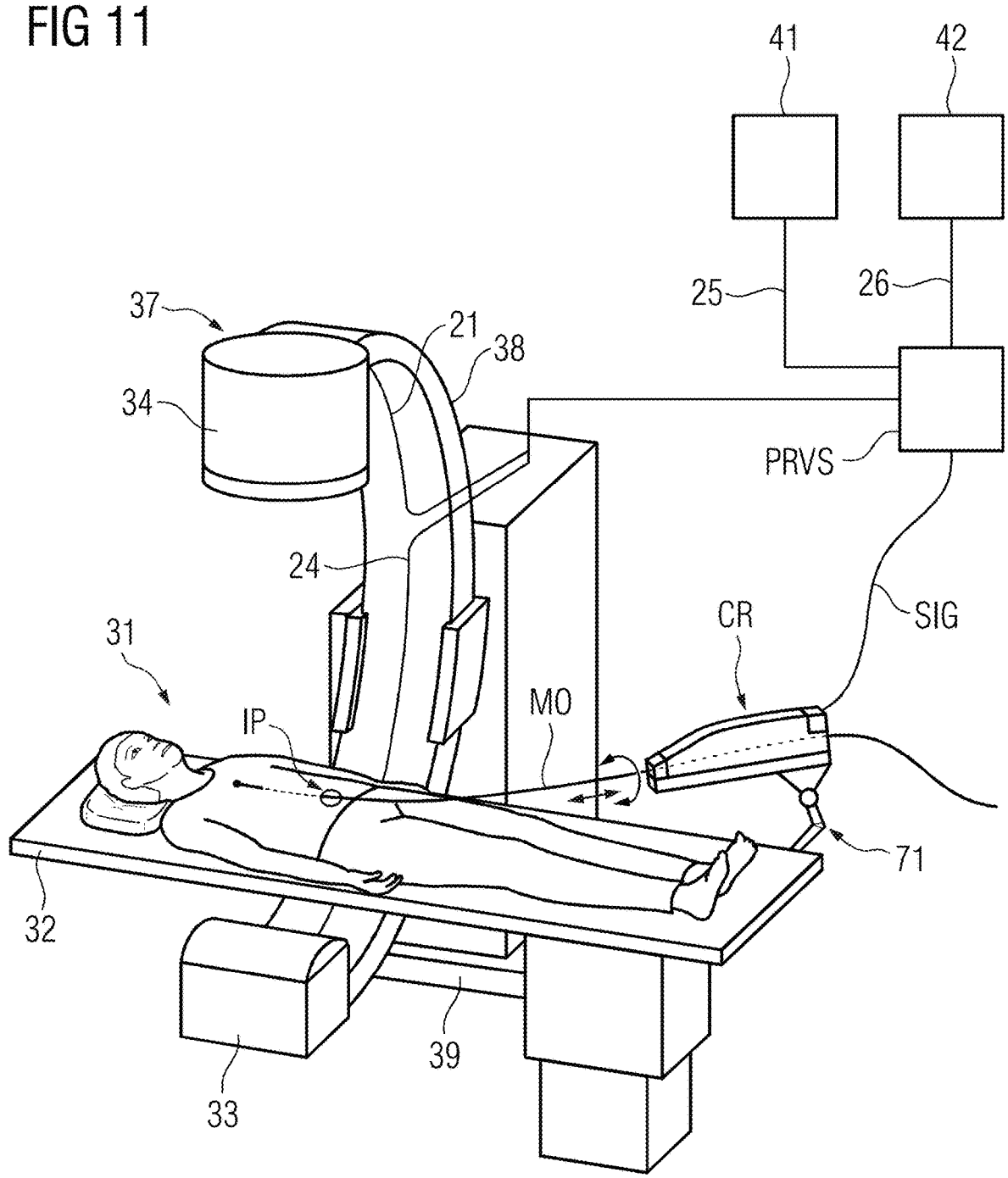

FIG. 11 is a schematic representation of a further embodiment of a proposed system. The system may, for example, include a movement apparatus CR for robotic movement of the medical object MO. The movement apparatus CR may, for example, take the form of a catheter robot (e.g., for remote manipulation of the medical object MO). In an operating state of the system, the medical object MO may be positioned at least in part in the hollow organ of the examination object 31. For example, in the operating state of the system, the medical object MO may be inserted via an insertion lock at an insertion point IP into the examination object 31 positioned on the patient positioning apparatus 32 (e.g., into the hollow organ HO of the examination object 31). The movement apparatus CR may be fastened (e.g., movably) via a fastening element 71 (e.g., a stand and/or robot arm) on the patient positioning apparatus 32. The movement apparatus CR may be configured to hold and/or move the medical object MO by force transfer. The movement apparatus CR may, for example, be configured to move the medical object MO positioned therein translationally at least along a lengthwise direction of the medical object MO. The movement apparatus CR may be configured to rotate the medical instrument MO about the lengthwise direction. Alternatively or additionally, the movement apparatus CR may be configured to control a movement of at least part of the medical object MO (e.g., a distal portion of the medical object MO). The movement apparatus CR may further be configured to deform the medical object MO (e.g., the distal portion) in defined manner (e.g., via a Bowden cable within the medical object MO).

The provision unit PRVS may be configured to provide the at least one procedure parameter PP to the movement apparatus CR (e.g., via a signal SIG). The movement apparatus CR may be configured to move the medical object MO based on the at least one procedure parameter PP.

Figure 12:
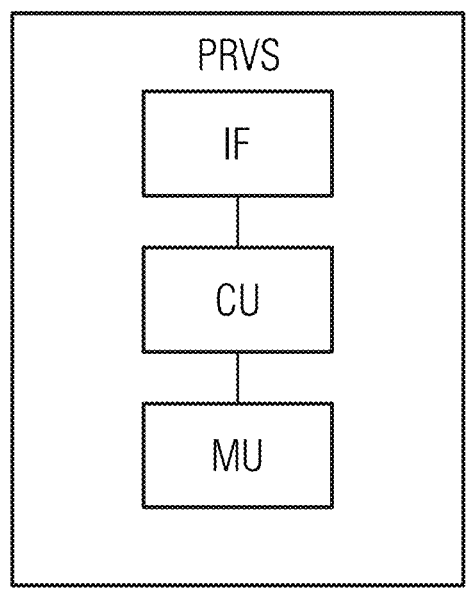
FIG. 12 shows a schematic representation of a provision unit.

FIG. 12 is a schematic representation of a provision unit PRVS. The provision unit PRVS may, for example, include a computing unit CU, a memory unit MU, and/or an interface IF. The provision unit PRVS may be configured to carry out a method for providing PROV-PP at least one procedure parameter, by the interface IF, the computing unit CU, and/or the memory unit MU being configured to carry out the corresponding method acts. For example, the interface IF may be configured to receive the at least one intraprocedural projection map iPR and to provide PROV-PP the at least one procedure parameter PP. The computing unit CU and/or the memory unit MU may be configured to apply the trained function TF to the at least one intraprocedural projection map iPR in order to provide the at least one procedure parameter PP as output data.

Figure 13:
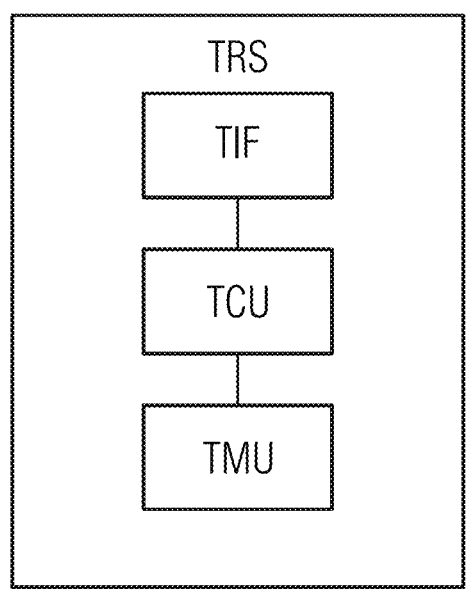
FIG. 13 shows a schematic representation of a training unit.

FIG. 13 is a schematic representation one embodiment of a training unit TRS. The training unit TRS may, for example, include a training interface TIF, a training memory unit TMU, and/or a training computing unit TCU. The training unit TRS may be configured to carry out a computer-implemented method for providing PROV-TF a trained function TF, a further computer-implemented method for providing PROV-TF a trained function, a computer-implemented method for providing PROV-NN1 a first neural network NN1 and/or a computer-implemented method for providing PROV-NN2 a second neural network NN2 by the training interface TIF, the training memory unit TMU, and/or the training computing unit TCU being configured to carry out the corresponding method acts.

The schematic representations contained in the described figures do not depict any scale or size ratios.

The methods and apparatuses described in detail above are merely embodiments that may be modified in the most varied manner by a person skilled in the art without departing from the scope of the invention. Further, use of the indefinite article "a" does not rule out the possibility of a plurality of the features in question also being present. Likewise, the terms "unit" and "element" do not rule out the possibility of the components in question consisting of a plurality of interacting subcomponents that may optionally also be spatially distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for providing at least one procedure parameter, the method comprising:
    acquiring at least one intraprocedural projection map that maps a hollow organ of an examination object with at least one medical object positioned in the hollow organ;
    applying a trained function to the at least one intraprocedural projection map as input data;
    adjusting at least one parameter of the trained function based on a simulation of a virtual positioning of at least one medical training object in a training hollow organ and of hemodynamics in the training hollow organ that are influenced by the at least one medical training object; and
    providing the at least one procedure parameter as output data of the trained function,
    wherein the at least one procedure parameter includes a movement specification for the at least one medical object.

2. The method of claim 1, wherein the at least one intraprocedural projection map maps a plurality of medical objects that are positioned in the hollow organ, and
    wherein the at least one procedure parameter includes a movement specification for the plurality of medical objects.

3. The method of claim 1, wherein the at least one medical object comprises a microcatheter, a coil implant, or the microcatheter and the coil implant.

4. The method of claim 1, wherein the hollow organ has an aneurysm, vessel malformation, or aneurysm and vessel malformation,
    wherein one or more procedure parameters of the at least one procedure parameter includes a movement specification for inserting the at least one medical object into the aneurysm, the vessel malformation, or the aneurysm and the vessel malformation.

5. The method of claim 1, further comprising:
    receiving a preprocedural data set that maps hemodynamics in the hollow organ; and
    applying the trained function to the preprocedural data set as input data.

6. The method of claim 5, wherein the trained function comprises a first neural network and a second neural network,
    wherein the method further comprises:
        applying the first neural network to the preprocedural data set and the at least one intraprocedural projection map as input data, such that a synthetic data set is provided, wherein synthetic data set maps simulated hemodynamics in the hollow organ with at least one medical object virtually positioned therein; and
        applying the second neural network to the synthetic data set as input data, such that the at least one procedure parameter is provided.

7. The method of claim 1, further comprising receiving a material parameter, an operating parameter, or the material parameter and the operating parameter regarding the at least one medical object,
    wherein the input data is also based on the material parameter, operating parameter, or the material parameter and the operating parameter.

8. The method of claim 1, wherein the movement specification specifies a velocity, an acceleration, a force, or any combination thereof for the at least one medical object.

9. The method of claim 1, wherein the acquiring and the applying are carried out repeatedly until a termination condition occurs.

10. The method of claim 1, further comprising providing the at least one procedure parameter to:
    a display unit for display of a graphical representation of the movement specification;
    a movement apparatus for robotic movement of the at least one medical object, the movement apparatus being configured to control a movement of the at least one medical object based on the at least one procedure parameter; or
    a combination thereof.

11. The method of claim 1, wherein the trained function includes a neural network, wherein the method further comprises providing the neural network, providing the neural network comprising:

receiving a preprocedural training data set that maps the hemodynamics in the training hollow organ of a training examination object;

receiving a synthetic comparison data set that maps the simulated hemodynamics in the training hollow organ with the at least one medical training object virtually positioned therein;

receiving the at least one intraprocedural training projection map that maps the training hollow organ with the at least one medical training object positioned therein, or providing the at least one intraprocedural training projection map by a virtual projection of the synthetic comparison data set;

providing a synthetic training data set, the providing of the synthetic training data set comprising applying the neural network to the input data that is based on at least one intraprocedural training projection map and the preprocedural training data set;

adjusting at least one parameter of the neural network based on a comparison between the synthetic training data set and the synthetic comparison data set; and providing the neural network.

12. The method of claim 1, wherein the trained function includes a neural network, and wherein the method further comprises:

providing the neural network, providing the neural network comprising:

receiving a preprocedural training data set that maps the hemodynamics in the training hollow organ of a training examination object;

providing a synthetic comparison data set as output data of a simulation of the virtual positioning of the at least one medical training object in the training hollow organ, wherein the simulation is based on at least one training procedure parameter that includes the movement specification for the at least one medical training object, and the preprocedural training data set as the input data;

adjusting at least one parameter of the neural network by supervised learning based on the input data and the output data of the simulation; and providing the neural network.

13. The method of claim 12, further comprising receiving a training material parameter, a training operating parameter, or the training material parameter and the training operating parameter regarding the at least one medical training object, wherein the input data of the simulation is also based on the training material parameter, the training operating parameter, or the training material parameter and the training operating parameter.

14. The method of claim 1, further comprising providing the trained function, providing the trained function comprising:

providing a first neural network, the providing of the first neural network comprising:

receiving a preprocedural training data set that maps the hemodynamics in the training hollow organ of a training examination object;

receiving a first synthetic comparison data set that maps the simulated hemodynamics in the training hollow organ with the at least one medical training object virtually positioned therein;

receiving at least one intraprocedural training projection map that maps the training hollow organ with the at least one medical training object positioned therein, or providing the at least one intraprocedural training projection map by a virtual projection of the synthetic comparison data set;

providing a synthetic training data set, the providing of the synthetic training data set comprising applying the first neural network to the input data that is based on the at least one intraprocedural training projection map and the preprocedural training data set;

adjusting at least one parameter of the first neural network based on a comparison between the synthetic training data set and the synthetic comparison data set; and providing the first neural network providing a second neural network, the providing of the second neural network comprising:

providing a second synthetic comparison data set as output data of the simulation of the virtual positioning of the at least one medical training object in the training hollow organ, wherein the simulation is based on at least one training procedure parameter that includes the movement specification for the at least one medical training object, and the preprocedural training data set as input data;

adjusting at least one parameter of the second neural network by supervised learning based on the input data and the output data of the simulation; and providing the second neural network; and providing the trained function comprising the first neural network and the second neural network, wherein the trained function is configured to:

be applied to the preprocedural training data set and the at least one intraprocedural training projection map as input data; and provide the at least one training procedure parameter as output data.

15. The method of claim 1, further comprising providing the trained function, providing the trained function comprising:

receiving the input data comprising:

at least one intraprocedural training projection map that maps the training hollow organ with the at least one medical training object positioned therein; or a synthetic comparison data set that maps the simulated hemodynamics in the training hollow organ with the at least one medical training object virtually positioned therein, wherein the at least one intraprocedural training projection map is provided by a virtual projection of the synthetic comparison data set;

adjusting at least one parameter of the trained function via reinforcement learning, such that a reward value is maximized, the adjusting comprising:

providing at least one training procedure parameter;

simulating a virtual positioning of the at least one medical training object in the training hollow organ based on the at least one training procedure parameter and the input data;

simulating the hemodynamics in the training hollow organ, the hemodynamics being influenced by the at least one medical training object in the virtual position;

determining the reward value based on:

a packing density of the at least one medical training object in the training hollow organ;

a probability of rupture of the training hollow organ by the at least one medical training object;

a probability of occlusion of the training hollow organ by the at least one medical training object; or any combination thereof, wherein the trained function is configurable to provide the at least one training procedure parameter having a maximum reward value as output data by adjustment of the at least one parameter; and providing the trained function.

16. The method of claim 15, further comprising receiving a preprocedural training data set that maps the hemodynamics in the training hollow organ of a training examination object,
wherein the input data of the trained function is also based on the preprocedural training data set.

17. The method of claim 1,
wherein acquiring the at least one intraprocedural projection map comprises capturing, by an imaging unit, the at least one intraprocedural projection map and providing the at least one intraprocedural projection map to a provision unit, and wherein providing the at least one procedure parameter as the output data of the trained function comprises providing, by the provision unit, the at least one procedure parameter as the output data of the trained function.

18. The method of claim 17, further comprising:
providing, by the provision unit, the at least one procedure parameter to a display unit, a movement apparatus, or the display unit and the movement apparatus,
wherein the display unit is configured to display a graphical representation of the movement specification, and
wherein the movement apparatus is configured to move the at least one medical object based on the at least one procedure parameter.

* * * * *